(12) United States Patent
Khatau (10) Patent No.: US 11,413,257 B2
(45) Date of Patent: Aug. 16, 2022

(54) METHODS FOR PREPARING CURCUMINOID COMPOSITIONS

(71) Applicant: LODAAT PHARMACEUTICALS, Oak Brook, IL (US)

(72) Inventor: Rajiv Khatau, Oak Brook, IL (US)

(73) Assignee: LODAAT PHARMACEUTICALS, Oak Brook, IL (US)

(*) Notice: Subject to any disclaimer, the term of this patent is extended or adjusted under 35 U.S.C. 154(b) by 0 days.

(21) Appl. No.: 16/765,533

(22) PCT Filed: Nov. 20, 2018

(86) PCT No.: PCT/US2018/062038
§ 371 (c)(1),
(2) Date: May 20, 2020

(87) PCT Pub. No.: WO2019/104050
PCT Pub. Date: May 31, 2019

(65) Prior Publication Data
US 2020/0306205 A1 Oct. 1, 2020

Related U.S. Application Data

(60) Provisional application No. 62/590,803, filed on Nov. 27, 2017.

(51) Int. Cl.
*A61K 9/14* (2006.01)
*A61K 31/12* (2006.01)

(52) U.S. Cl.
CPC ............... *A61K 31/12* (2013.01); *A61K 9/14* (2013.01); *A61K 2236/33* (2013.01)

(58) Field of Classification Search
None
See application file for complete search history.

(56) References Cited

U.S. PATENT DOCUMENTS

| | | | | |
|---|---|---|---|---|
| 7,745,558 B2* | 6/2010 | Choi | ............. | G01N 33/743 527/300 |
| 2004/0028751 A1* | 2/2004 | Mae | ................ | A23L 33/10 424/684 |
| 2005/0106307 A1* | 5/2005 | Kikuchi | ............. | A23L 5/25 426/615 |
| 2008/0193573 A1* | 8/2008 | Gow | ................ | A61P 25/28 424/756 |
| 2008/0226755 A1 | 9/2008 | Antony | | |
| 2010/0092406 A1* | 4/2010 | Perez-Davidi | ......... | A61K 36/28 424/48 |
| 2011/0190399 A1* | 8/2011 | Kar | ................. | A61P 1/16 514/679 |
| 2012/0058208 A1* | 3/2012 | Jacob | ............... | A61K 31/12 424/756 |
| 2014/0056828 A1 | 2/2014 | Pather et al. | | |
| 2014/0056829 A1* | 2/2014 | Pather | ............... | A61P 29/00 424/59 |
| 2014/0099390 A1 | 4/2014 | Antony | | |
| 2015/0258066 A1 | 9/2015 | Niwa et al. | | |
| 2016/0089343 A1* | 3/2016 | Nathan | .............. | A61K 9/0058 514/679 |
| 2016/0151440 A1 | 6/2016 | Gopi | | |
| 2016/0174598 A1* | 6/2016 | Hirt | ................. | A23L 2/39 426/590 |
| 2016/0287514 A1* | 10/2016 | Cordoliani | ....... | A61K 31/192 |
| 2016/0346339 A1* | 12/2016 | Finley | ............. | A61K 31/355 |

FOREIGN PATENT DOCUMENTS

WO    WO 2019/104050 A1    5/2019

OTHER PUBLICATIONS

Netafim, Mesh vs. Micron Comparison Chart, retrieved online Aug. 13, 2015 (Year: 2015).*
Popuri et al., *International Journal of innovative Research & Studies*, 2(5): 289-299 (2013).
The United States Patent and Trademark Office, International Search Report in International Application No. PCT/US2018/062038 (dated Feb. 4, 2019).
The United States Patent and Trademark Office, Written Opinion in International Application No. PCT/US2018/062038 (dated Feb. 4, 2019).
Cuomo et al., *J. Nat. Prod.* 2011, 74, 4, 664-669 (2011).

* cited by examiner

*Primary Examiner* — Jennifer A Berrios
(74) *Attorney, Agent, or Firm* — Neal, Gerber & Eisenberg LLP; Kevin A. O'Connor

(57) ABSTRACT

The invention relates to methods for preparing dispersible curcuminoid compositions.

18 Claims, 4 Drawing Sheets

METHODS FOR PREPARING CURCUMINOID COMPOSITIONS

CROSS-REFERENCE TO RELATED APPLICATIONS

This application is a National Stage Entry of International Application Number PCT/US2018/062038, which was filed on Nov. 20, 2018 and claimed priority to U.S. Provisional Application No. 62/590,803, which was filed on Nov. 27, 2017. The contents of each of the aforementioned applications are incorporated herein by reference in their entireties.

BACKGROUND OF THE INVENTION

Field of the Invention

This disclosure relates generally to curcuminoid compositions. More particularly, the present disclosure relates to methods for preparing dispersible curcuminoid compositions.

Description of Related Art

Figure 1:
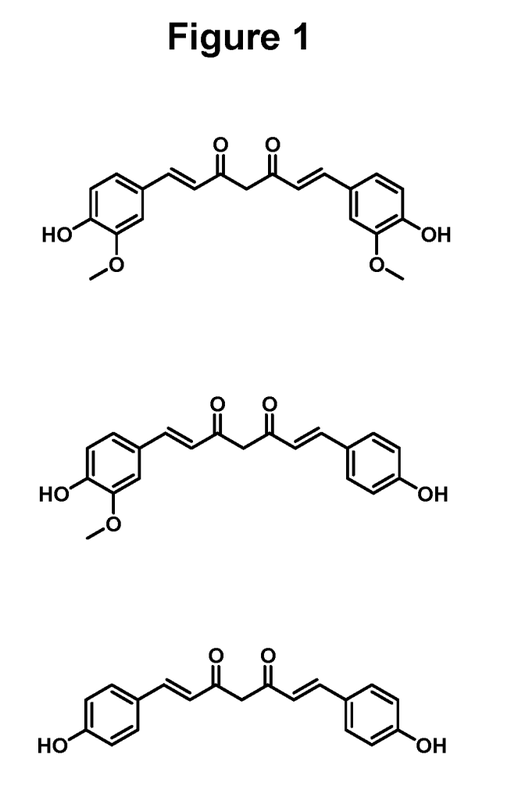
FIG. 1 is a schematic showing the chemical structures of curcumin (top), demethoxycurcumin (middle), and bisdemethocycurcumin (bottom).

Curcuminoids are the family of natural phenols responsible for the distinctive yellow color of turmeric (*Curcuma longa*) (see FIG. 1). Curcuminoids are widely used in commercial goods as an herbal supplement, cosmetics ingredient, food flavoring, and food coloring.

Conventional methods for producing curcuminoids such as curcumin (the principal curcuminoid of turmeric) include a single extraction step from dried turmeric rhizomes followed by purification via column chromatography. See, e.g., Kulkarni et al., "Extraction and purification of curcuminoids from Turmeric (*Curcuma longa* L.)," IJPPT 1(2):81-84 (2017).

Curcuminoids and in particular curcumin are poorly water-soluble. Accordingly, conventional curcuminoid extracts aggregate when mixed with aqueous liquids such as water or milk, complicating or preventing incorporation of curcuminoids into comestibles (e.g., for use as a herbal supplement).

Accordingly, there remains a need for a process for preparing a curcuminoid composition that is highly dispersible in water.

SUMMARY OF THE INVENTION

It is against the above background that the present invention provides certain advantages and advancements over the prior art.

Although this invention as disclosed herein is not limited to specific advantages or functionalities (such for example, preparing a curcuminoid composition highly dispersible in water), the invention provides a method for preparing a dispersible curcuminoid composition, comprising:
 (a) providing a particulate curcuminoid source comprising turmeric root, the source having an average particle size within the range of about 1 mm to about 10 mm;
 (b) extracting curcuminoids from the particulate source into an extraction solvent;
 (c) removing at least a portion of the extraction solvent to provide a curcuminoid slurry;
 (d) drying the curcuminoid slurry to provide a dried curcuminoid composition;
 (e) comminuting the dried curcuminoid composition; and
 (f) blending the comminuted curcuminoid composition with an emulsifier to prepare the dispersible curcuminoid composition.

In one aspect of the methods disclosed herein,
 (a) the curcuminoid source further comprises curcumin, demethoxycurcumin, bisdemethoxycurcumin, or a combination thereof; and
 (b) the total amount of curcumin, demethoxycurcumin, and/or bisdemethoxycurcumin is at least about 1 wt. %, or at least about 3 wt. %, or at least about 5 wt. % of the curcuminoid source.

In one aspect of the methods disclosed herein,
 (a) curcumin comprises about 75 wt. % to about 95 wt. % of the total curcuminoids present in the curcuminoid source;
 (b) demethoxycurcumin comprises about 1 wt. % to about 20 wt. % of the total curcuminoids present in the curcuminoid source; and
 (c) bisdemethoxycurcumin comprises about 0.5 wt. % to about 15 wt. % of the total curcuminoids present in the curcuminoid source.

In one aspect of the methods disclosed herein, the particulate curcuminoid source has a D90 of at least about 1 mm, or about 2.5 mm, or about 5 mm.

In one aspect of the methods disclosed herein, the extraction solvent is ethyl acetate.

In one aspect of the methods disclosed herein, removing at least a portion of the extraction solvent comprises evaporating a portion of the extraction solvent to provide the curcuminoid slurry.

In one aspect, the methods disclosed herein further comprise mixing the curcuminoid slurry with a non-polar wash solvent; and removing the wash solvent from the slurry.

In one aspect of the methods disclosed herein, the curcuminoid slurry comprises at least about 10 wt. %, at least about 15 wt. %, or at least about 20 wt. % curcuminoids.

In one aspect of the methods disclosed herein, drying is performed at a temperature within the range of about 50° C. to about 100° C., or about 60° C. to about 90° C., or about 70° C. to about 80° C.

In one aspect of the methods disclosed herein, the dried curcuminoid composition comprises at least about 10 wt. %, at least about 15 wt. %, or at least about 20 wt. % curcuminoids.

In one aspect, the methods disclosed herein further comprise filtering the dried curcuminoid composition.

In one aspect of the methods disclosed herein, the comminution is performed in a bead mill.

In one aspect of the methods disclosed herein, the comminuted curcuminoid composition has average particle size within the range of about 5 nm to about 200 nm, or about 20 nm to about 150 nm, or about 40 nm to about 75 nm.

In one aspect of the methods disclosed herein, the comminuted curcuminoid composition is further blended with a filler.

In one aspect of the methods disclosed herein, the filler comprises maltodextrin having an average particle size within the range of about 20 nm to about 200 nm, or about 40 nm to about 150 nm, or about 60 nm to about 100 nm.

The invention also provides a dispersible curcuminoid composition, prepared by the methods disclosed herein.

In one aspect, the composition disclosed herein has a density within the range of about 0.1 g/ml to about 1.5 g/ml, or about 0.2 g/ml to about 1 g/ml, or about 0.3 g/ml to about 0.7 g/ml.

In one aspect of the compositions disclosed herein, the total amount of curcuminoids present in the dispersible composition is within the range of about 2 wt. % to about 40 wt. %, or about 5 wt. % to about 30 wt. %, or about 5 wt. % to about 20 wt. %.

In one aspect of the compositions disclosed herein, curcumin is present in the dispersible composition in an amount within the range of about 1 wt. % to about 30 wt. %, or about 5 wt. % to about 25 wt. %, or about 10 wt. % to about 20 wt. %.

In one aspect of the compositions disclosed herein, the dispersible composition comprises:
  (a) a total amount of curcuminoids within the range of about 1 wt. % to about 30 wt. % (e.g., about 10 wt. % to about 20 wt. %); and
  (b) a filler (e.g., maltodextrin), present in an amount within the range of about 70 wt. % to about 99 wt. % (e.g., about 80 wt. % to about 90 wt. %).

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Numerous references have been made to patents and printed publications throughout this specification. Each of the cited references and printed publications are individually incorporated herein by reference in their entirety.

Furthermore, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Figure 2:
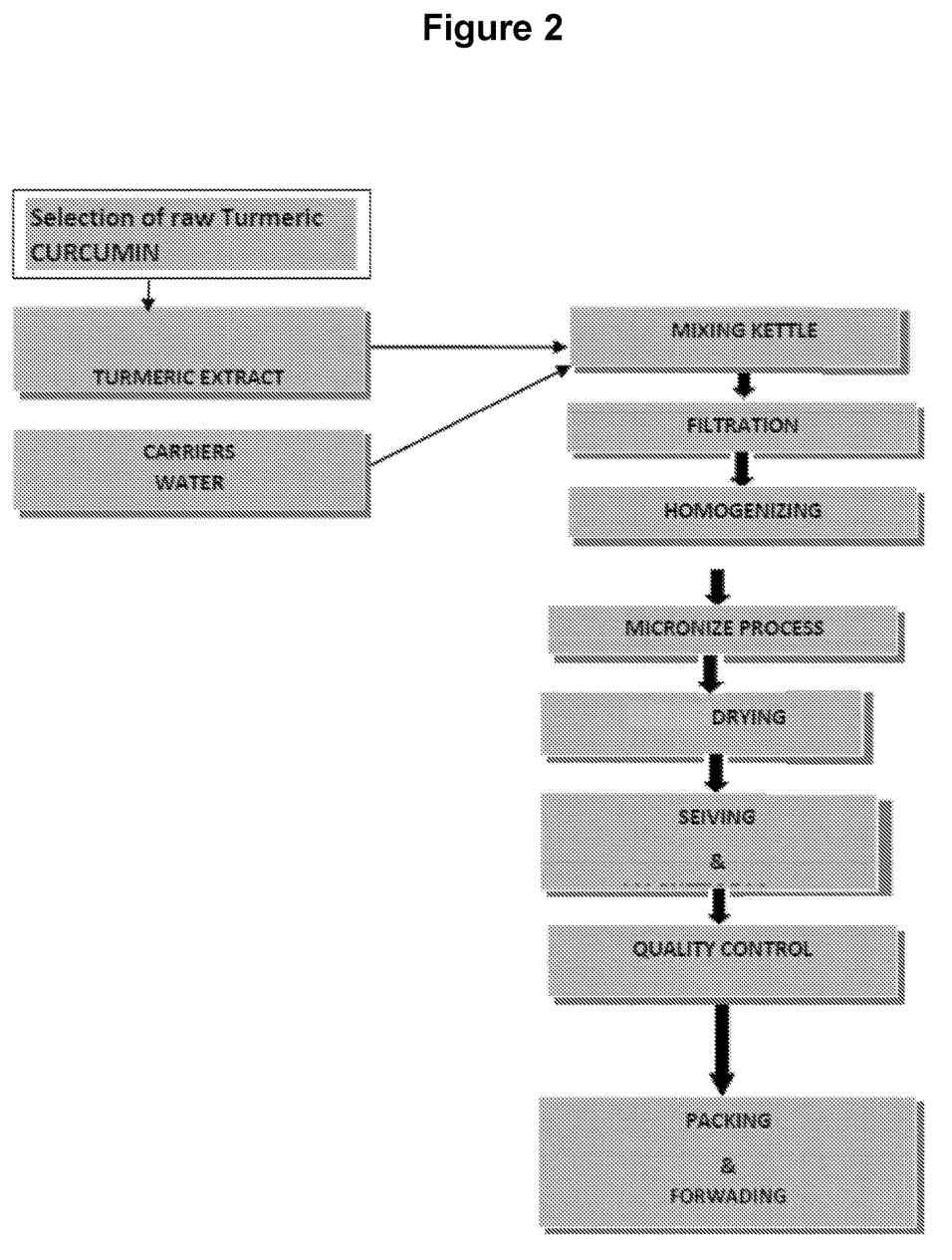
FIG. 2 is a flowchart of a process for preparing a curcuminoid composition according to one embodiment of the disclosure.
Figure 3:
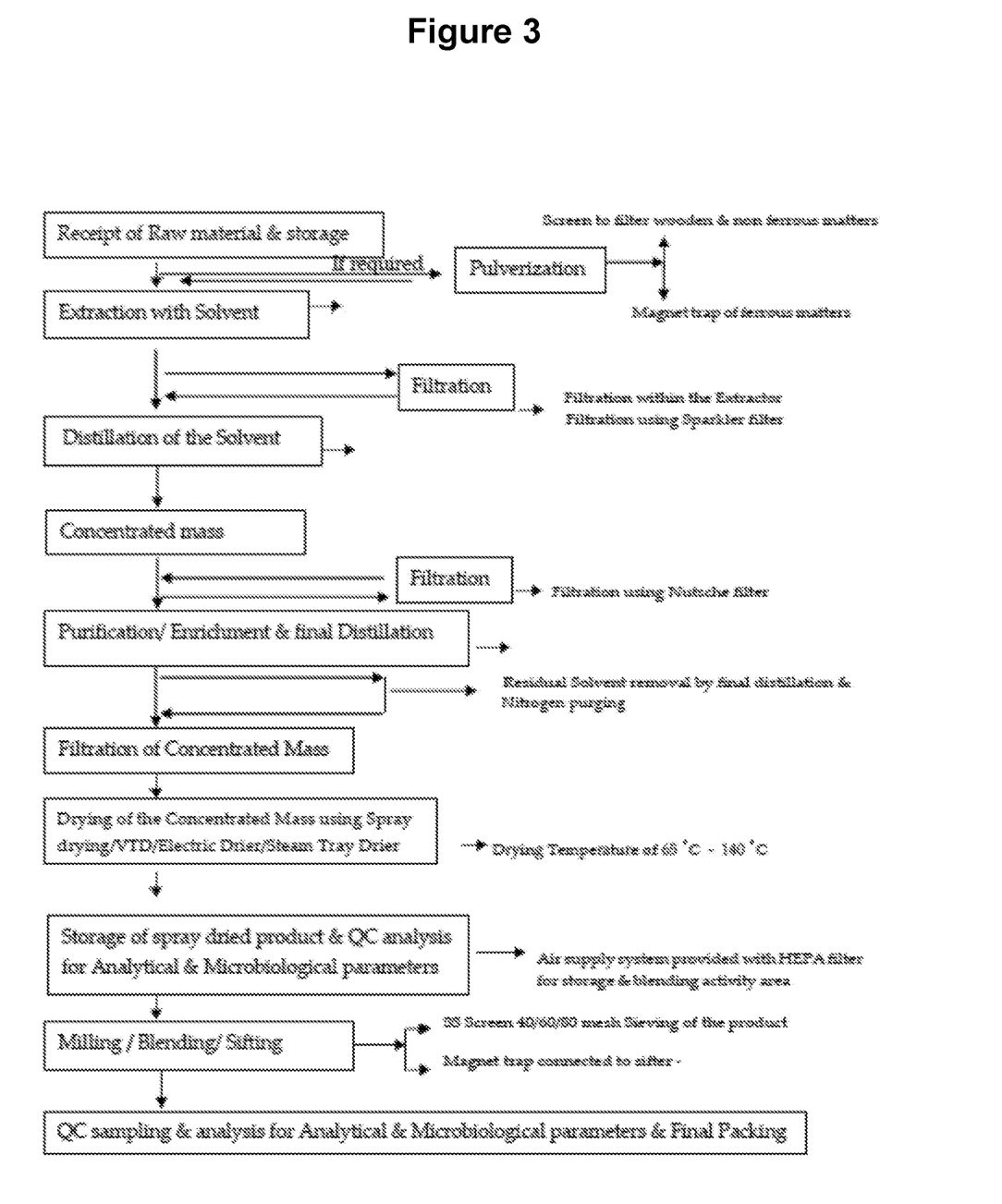
FIG. 3 is a flowchart of a process for preparing a curcuminoid composition according to one embodiment of the disclosure.
Figure 4:
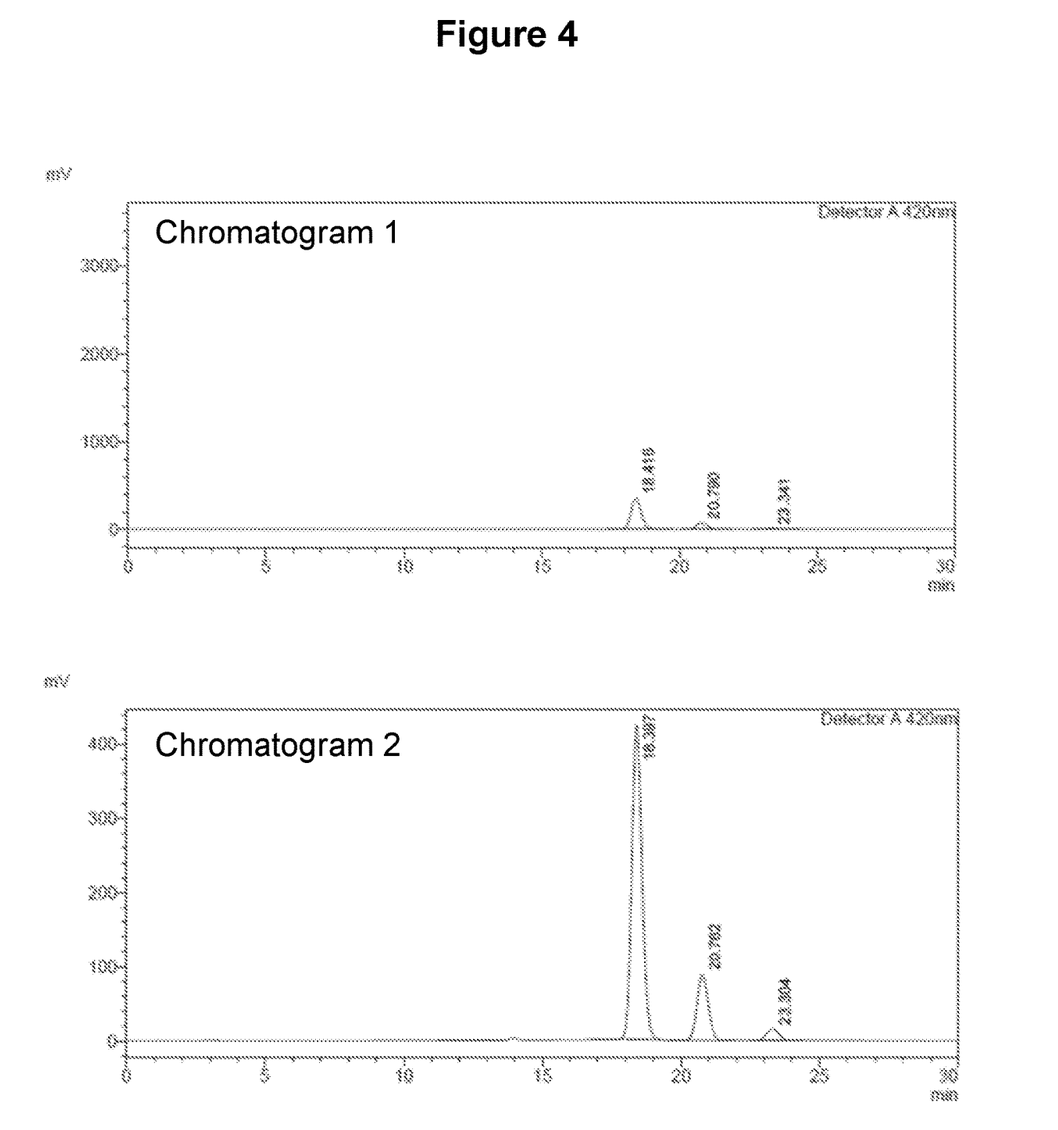
FIG. 4 is a set of chromatograms ($\lambda_{abs}$=420 nm) obtained by high-performance liquid chromatography (HPLC) for curcuminoid compositions prepared according to one embodiment of the disclosure. See Example 1.

The disclosure relates to methods for preparing a curcuminoid composition that include preparing a curcuminoid slurry from a curcuminoid source, drying the slurry, comminuting the dried curcuminoids, and blending the comminuted curcuminoids with an emulsifier. See, e.g., FIGS. 2-3. The disclosure demonstrates that the method provides a curcuminoid composition that is dispersible in aqueous liquids such as, for example, water. The disclosure demonstrates that a relatively uniform suspension of such compositions in aqueous liquid can be easily formed. The disclosure demonstrates that such curcuminoid compositions can remain suspended in water for an extended period of time relative to conventionally prepared compositions.

As used herein, the term "dispersible" refers to the ability of a composition to readily form a suspension in water upon agitation (e.g., shaking or stirring). As used herein, the term "suspension" refers to a heterogeneous mixture of solid particles and water. The person of ordinary skill in the art will appreciate that, while a suspension is heterogeneous, the individual particles of a suspension may be discernible or indiscernible to the naked eye. One or more components of a dispersible composition can be poorly water-soluble, or even highly water-soluble.

Accordingly, one aspect of the disclosure is a method for preparing a dispersible curcuminoid composition suitable, for example, for suspension in aqueous liquids for comestible applications. The method comprises providing a particulate curcuminoid source. The curcuminoid source comprises turmeric root, and has an average particle size within the range of about 1 mm to about 10 mm. The method further comprises extracting curcuminoids from the particulate source into an extraction solvent; and removing at least a portion of the extraction solvent to provide a curcuminoid slurry. The method further comprises drying the curcuminoid slurry to provide a dried curcuminoid composition, comminuting the dried composition, and blending the comminuted composition with an emulsifier to provide the dispersible curcuminoid composition.

As noted above, the method comprises extracting curcuminoids from a particulate curcuminoid source comprising turmeric (*Curcuma longa*) root. As used herein, the term "curcuminoid" includes naturally occurring linear diarylheptanoids (e.g., in *Curcuma longa*), and any derivative thereof. For example, in certain embodiments as otherwise described herein, the curcuminoid source comprises one or more curcuminoids selected from curcumin, demethoxycurcumin, and bisdemethoxycurcumin.

In certain embodiments as otherwise described herein, the curcuminoid source comprises at least about 1 wt. % curcuminoids on a dry-weight basis. For example, in certain such embodiments, the curcuminoid source comprises at least 1.5 wt. %, or at least about 2 wt. %, or at least about 2.5 wt. %, or at least about 3 wt. %, or at least about 3.5 wt. %, or at least about 4 wt. %, or at least about 4.5 wt. %, or at least about 5 wt. % curcuminoids. In certain such embodiments, the curcuminoid source comprises curcuminoids in an amount within the range of about 2 wt. % to about 10 wt. %, or about 3 wt. % to about 9 wt. %, or about 4 wt. % to about 8 wt. %, or about 5 wt. % to about 7 wt. % on a dry-weight basis.

As noted above, the average particle size of the curcuminoid source is within the range of about 1 mm to about 10 mm. In certain embodiments as otherwise described herein, the particulate source is comminuted plant matter. The person of ordinary skill in the art will appreciate that plant matter can be comminuted by a variety of means. For example, in certain such embodiments, providing the particulate curcuminoid source comprises comminuting (e.g., by extruding, grinding, milling, or pulverizing) turmeric root into particles having an average size within the range of about 1 mm to about 10 mm.

In certain embodiments as otherwise described herein, the particulate curcuminoid source has a D90 value of at least about 1 mm. As used herein, the "D90 value" of a plurality of particles refers to the particle size at which 90% of the mass of the plurality comprises particles less than the value. For example, in certain embodiments as otherwise described herein, the particulate curcuminoid source has a D90 value of at least about 1.5 mm, or at least about 2 mm, or at least about 2.5 mm, or at least about 3 mm, or at least about 3.5 mm, or at least about 4 mm, or at least about 4.5 mm, or at least about 5 mm. In one example, in certain embodiments as otherwise described herein, providing a particulate curcuminoid source having a D90 value of at least about 1 mm further comprises sieving turmeric root (e.g., before comminuting the turmeric root) over a screen having a pore size within the range of about 3.5 mesh to about 60 mesh.

As noted above, curcuminoids are extracted from the particulate source into an extraction solvent. In certain embodiments as otherwise described herein, the extraction solvent is an organic solvent. For example, in certain such embodiments, the extraction solvent is ethyl acetate. In certain embodiments as otherwise described herein, the extraction solvent and the particulate source are mixed (e.g., in a vertical extractor) for a period of time within the range of about 1 hour to about 10 hours. For example, in certain such embodiments, the extraction solvent and the particulate source are mixed for a period of time within the range of about 2 hours to about 9 hours, or about 3 hours to about 8 hours, or about 3 hours to about 7 hours, or about 3 hours to about 6 hours, or about 3 hours to about 5 hours. Following mixing (e.g., for a period of time sufficient to extract curcuminoids form the particulate source; e.g., for about 3-5 hours), the extraction solvent can be separated from the particulate source. For example, in certain embodiments as otherwise described herein, the extraction solvent is separated from the particulate source by sparkler filtration.

In certain embodiments of the methods as otherwise described herein, extracting curcuminoids from the particulate source into an extraction solvent comprises stirring the particulate curcuminoid source (e.g., comminuted turmeric root) with an extraction solvent. In certain embodiments as otherwise described herein, curcuminoids are extracted from the particulate source over three extraction steps (i.e., each step including mixing the particulate source with extraction solvent, and separating the extraction solvent). For example, in certain embodiments, the extraction includes a first extraction step, a second extraction step, and a third extraction step, wherein the extraction solvent of each step is ethyl acetate. In certain such embodiments, the volume of the extraction solvent of the first extraction step is greater than the volume of extraction solvent of the second extraction step, and the volume of extraction solvent of the second extraction step is greater than the volume of extraction solvent of the third extraction step. In certain such embodiments, the volume of extraction solvent used in the first extraction step (i.e., in liters) is about 4 to about 6 times greater than the mass of particulate source material (i.e., in kilograms). In certain such embodiments, the volume of extraction solvent used in the second extraction step is about 3 to about 5 times greater than the mass of particulate source material. In certain such embodiments, the volume of extraction solvent used in the third extraction step is about 2 to about 4 times greater than the mass of particulate source material.

As noted above, at least a portion of the extraction solvent is removed to provide a curcuminoid slurry. As used herein, the term "slurry" describes a solid-liquid mixture. The person of ordinary skill in the art will appreciate that a slurry of curcuminoids and extraction solvent can include curcuminoid particles and dissolved curcuminoids. In certain embodiments as otherwise described herein, removing a portion of the extraction solvent comprises evaporating a portion of the extraction solvent. For example, in certain such embodiments at least a portion of the extraction solvent is evaporated using a thin-film evaporator. In certain such embodiments, the extraction solvent is evaporated over a period of time within the range of about 5 hours to about 50 hours, or about 10 hours to about 40 hours, or about 15 hours to about 35 hours, or about 20 hours to about 30 hours, or about 22 hours to about 28 hours. In certain embodiments as otherwise described herein, at least about 90 wt. % of the extraction solvent is removed (e.g., by thin-film evaporation) to provide the curcuminoid slurry. For example, in certain such embodiments, at least about 92.5 wt. %, or at least about 95 wt. %, or at least about 97.5 wt. %, or at least about 98 wt. % of the extraction solvent is removed. In another example, in certain such embodiments, the amount of extraction solvent removed is within the range of about 90 wt. % to about 99 wt. %.

In certain desirable embodiments as otherwise described herein, the curcuminoid slurry (i.e., provided by evaporating at least a portion of the extraction solvent) comprises at least about 10 wt. % curcuminoids. For example, in certain such embodiments, the slurry comprises at least about 12.5 wt. %, or at least about 15 wt. %, or at least about 17.5 wt. %, or at least about 20 wt. % curcuminoids. In certain such embodiments, the slurry comprises curcuminoids in an amount within the range of about 10 wt. % to about 50 wt. %, or about 15 wt. % to about 50 wt. %, or about 20 wt. % to about 50 wt. %, or about 25 wt. % to about 50 wt. %, or about 10 wt. % to about 45 wt. %, or about 10 wt. % to about 40 wt. %, or about 10 wt. % to about 35 wt. %, or about 10 wt. % to about 30 wt. %, or about 10 wt. % to about 25 wt. %, or about 12.5 wt. % to about 40 wt. %, or about 15 wt. % to about 30 wt. %.

In certain embodiments as otherwise described herein, the curcuminoid slurry (i.e., provided by evaporating at least a portion of the extraction solvent) comprises at least about 5 wt. % curcumin. For example, in certain such embodiments, the slurry comprises at least about 7.5 wt. %, or at least about 10 wt. %, or at least about 12.5 wt. %, or at least about 15 wt. %, or at least about 17.5 wt. %, or at least about 20 wt. % curcumin. In certain such embodiments, the slurry comprises curcumin in an amount within the range of about 5 wt. % to about 45 wt. %, or about 5 wt. % to about 40 wt. %, or about 5 wt. % to about 35 wt. %, or about 5 wt. % to about 30 wt. %, or about 5 wt. % to about 25 wt. %, or about 10 wt. % to about 45 wt. %, or about 15 wt. % to about 45 wt. %, or about 20 wt. % to about 45 wt. %, or about 25 wt. % to about 45 wt. %, or about 10 wt. % to about 40 wt. %, or about 15 wt. % to about 35 wt. %, or about 20 wt. % to about 30 wt. %, or about 20 wt. % to about 25 wt. %.

In certain embodiments as otherwise described herein, the method includes washing the curcuminoid slurry. For example, in certain embodiments as otherwise described herein, the curcuminoid slurry (i.e., provided by evaporating at least a portion of the extraction solvent) is mixed with a wash solvent. In certain such embodiments, the wash solvent is a non-polar wash solvent such as, for example, hexane. In certain such embodiments, the curcuminoid slurry (e.g., including less than 10 wt. %, or less than 5 wt. %, or less than 1 wt. % of the extraction solvent) is mixed with a non-polar wash solvent (e.g., hexane) to remove non-curcuminoid materials (e.g., oils) from the slurry. In certain such embodiments, the slurry is mixed with wash solvent (e.g., hexane) in a ratio of about 1:0.5 (i.e., 1 kg slurry to 0.5 L of wash solvent) to about 1:2, or about 1:0.5 to about 1:1.5, or about 1:0.5 to about 1:1, or about 1:0.7 to about 1:0.9. After mixing the slurry and the wash solvent (i.e., for a period sufficient to dissolve at least a portion of the non-curcuminoid materials in the wash solvent), the wash solvent is removed, for example, by sparkler filtration.

As noted above, the method includes drying the curcuminoid slurry. In certain embodiments as otherwise described herein, drying the curcuminoid slurry comprises vacuum tray drying. Desirably, vacuum tray drying does not burn the curcuminoid slurry. In certain embodiments as otherwise described herein, the curcuminoid slurry is dried at a temperature within the range of about 50° C. to about 100° C. For example, in certain such embodiments, the curcuminoid slurry is dried at a temperature within the range of about 55° C. to about 95° C., or about 60° C. to about 90° C., or about 65° C. to about 85° C., or about 70° C. to about 80° C. In certain embodiments as otherwise described herein, the curcuminoid slurry is dried for a period of time within the range of about 1 hour to about 12 hours, or about 2 hours to about 11 hours, or about 3 hours to about 10 hours, or about 4 hours to about 9 hours, or about 5 hours to about 8 hours.

In certain desirable embodiments as otherwise described herein, the dried curcuminoid composition comprises at least about 10 wt. % curcuminoids. For example, in certain such embodiments, the dried composition comprises at least about 12.5 wt. %, or at least about 15 wt. %, or at least about 17.5 wt. %, or at least about 20 wt. % curcuminoids. In certain such embodiments, the dried composition comprises curcuminoids in an amount within the range of about 10 wt. % to about 50 wt. %, or about 15 wt. % to about 50 wt. %, or about 20 wt. % to about 50 wt. %, or about 25 wt. % to about 50 wt. %, or about 10 wt. % to about 45 wt. %, or about 10 wt. % to about 40 wt. %, or about 10 wt. % to about 35 wt. %, or about 10 wt. % to about 30 wt. %, or about 10 wt. % to about 25 wt. %, or about 12.5 wt. % to about 40 wt. %, or about 15 wt. % to about 30 wt. %.

In certain embodiments as otherwise described herein, the dried curcuminoid composition comprises at least about 5 wt. % curcumin. For example, in certain such embodiments, the dried composition comprises at least about 7.5 wt. %, or at least about 10 wt. %, or at least about 12.5 wt. %, or at least about 15 wt. %, or at least about 17.5 wt. %, or at least about 20 wt. % curcumin. In certain such embodiments, the dried composition comprises curcumin in an amount within the range of about 5 wt. % to about 45 wt. %, or about 5 wt. % to about 40 wt. %, or about 5 wt. % to about 35 wt. %, or about 5 wt. % to about 30 wt. %, or about 5 wt. % to about 25 wt. %, or about 10 wt. % to about 45 wt. %, or about 15 wt. % to about 45 wt. %, or about 20 wt. % to about 45 wt. %, or about 25 wt. % to about 45 wt. %, or about 10 wt. % to about 40 wt. %, or about 15 wt. % to about 35 wt. %, or about 20 wt. % to about 30 wt. %, or about 20 wt. % to about 25 wt. %.

In certain embodiments as otherwise described herein, the dried curcuminoid composition is filtered. For example, in certain such embodiments, the dried composition is filtered with a Nutsche filter.

As noted above, the method includes comminuting the dried curcumin composition. Advantageously, the present inventors have determined that the comminuted particles described herein can be suspended uniformly, and can remain suspended for relatively extended periods of time. In certain embodiments as otherwise described herein, the comminuted curcuminoid composition has an average particle size within the range of about 5 nm to about 200 nm. For example, in certain such embodiments, the comminuted curcuminoid composition has an average particle size within the range of about 15 nm to about 175 nm, or about 20 nm to about 150 nm, or about 30 nm to about 125 nm, or about 35 nm to about 100 nm, or about 40 nm to about 75 nm.

The person of ordinary skill in the art will appreciate that the dried curcuminoid composition can be comminuted by a variety of means. In some embodiments, the dried composition is comminuted by an extruder (e.g., a screw extruder or twin-screw extruder). In other embodiments, the dried composition is comminuted by a grinder (e.g., a blade grinder or a propeller grinder). In yet other embodiments, the dried composition is comminuted by a mill (e.g., a bead mill, a conical mill, a disk mill, or a hammer mill). For example, in certain embodiments as otherwise described herein, comminuting the dried curcuminoid composition comprises milling the dried composition in a bead mill, to an average particle size within the range of about 15 nm to about 100 nm.

In certain embodiments as otherwise described herein, the comminuted curcuminoid composition is further blended with a filler. For example, in certain embodiments as otherwise described herein, the comminuted curcuminoid composition is blended with a maltodextrin filler. In certain embodiments as otherwise described herein, the comminuted curcuminoid composition (e.g., having an average particle size within the range of about 15 nm to about 100 nm) is blended with a maltodextrin filler having an average particle size within the range of about 20 nm to about 200 nm, or about 40 nm to about 150 nm, or about 60 nm to about 100 nm. In certain embodiments as otherwise described herein, the filler can have emulgent properties.

Another aspect of the disclosure is a dispersible curcuminoid composition prepared by a method as otherwise described herein. In certain embodiments as otherwise described herein, the total amount of curcuminoids present in the dispersible composition is within the range of about 2 wt. % to about 40 wt. %. For example, in certain such embodiments, the total amount of curcuminoids present in the dispersible composition is within the range of about 2.5 wt. % to about 35 wt. %, or about 5 wt. % to about 30 wt. %, or about 5 wt. % to about 25 wt. %, or about 5 wt. % to about 20 wt. %.

In certain embodiments as otherwise described herein, the dispersible curcuminoid composition comprises a total amount of curcuminoids within the range of about 1 wt. % to about 30 wt. %, or about 10 wt. % to about 20 wt. % and a filler (e.g., maltodextrin), present in an amount within the range of about 70 wt. % to about 99 wt. %, or about 80 wt. % to about 90 wt. %.

The present inventors have determined that the dispersible curcuminoid compositions as otherwise described herein can be made using the comminuted dried curcuminoid composition and filler. In certain desirable embodiments, the comminuted composition and filler make up at least about 70 wt. % of the dispersible curcuminoid composition. For example, in certain embodiments as otherwise described herein, the one or more curcuminoids and filler make up at least about 75 wt. %, or at least about 80 wt. %, or at least about 85 wt. %, or at least about 90 wt. %, or at least about 95 wt. % of the dispersible composition.

In certain embodiments as otherwise described herein, the curcuminoids of the dispersible composition are relatively easily suspended in aqueous liquid (e.g., water). For example, in certain such embodiments, the curcuminoids of the dispersible composition can be suspended by agitation (e.g., shaking or stirring) for a period of time within the range of 10 seconds to about 2 minutes. In certain embodiments as otherwise described herein, the curcuminoids of the dispersible composition can remain suspended in aqueous liquid for relatively extended periods of time. For example, in certain such embodiments, the curcuminoids of the dispersible composition can remain suspended in a mixture of the dispersible composition and water (e.g., a mixture of water and the dispersible composition in relative amounts within the range of about 10:1 to about 30:1 by volume), for at least about 15 minutes (e.g., for at least about 30 minutes, or for at least about 45 minutes, or for at least about 1 hour).

The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1. Preparation of Dispersible Curcuminoid Composition 500 kg of Panangali-variety trumeric root was manually sorted to remove wood particles. The sorted material was shaken over a 40-mesh sieve for 3-4 hours to remove additional debris. The turmeric root was then pulverized in a grinding hammer mill for 3-4 hours to provide particles having an average particle size of 4.5±1 mm. The root particles were extracted in a vertical extractor with 2500 L of ethyl acetate for 4-5 hours, then with 2000 L of ethyl acetate for 4-5 hours and finally with 1500 L of ethyl acetate for 4-5 hours. After each extraction step, the extraction solvent was separated from the particulate material by sprinkler filtration and transferred to a distillation apparatus. About 99 wt. % of the extraction solvent was removed by evaporation in the distillation apparatus over 22-28 hours, providing 50-75 kg of a slurry of curcuminoids in residual ethyl acetate. The slurry was vacuum dried at a temperature of 70-80° C. for 5-8 hours, under about 1-2 kg of pressure. After vacuum drying, the material was filtered with a Nutsche filter for 2-3 hours. Chromatograms ($\lambda_{abs}$=420 nm) obtained by high-performance liquid chromatography (HPLC) for two independent samples of the died, filtered material are provided in FIG. 1. The peaks in each chromatogram around 18 minutes, minutes, and 23 minutes correspond to curcumin, demethoxycurcumin, and bisdemethoxycurcmin, respectively. Corresponding peak analysis data is provided in Tables 1 and 2, below.

TABLE 1

Peak Analysis Data - Chromatogram 1

| Peak | Retention Time (min) | Area | Height | Concentration (%) |
|---|---|---|---|---|
| 1 | 18.416 | 9104318 | 352475 | 78.503 |
| 2 | 20.790 | 2085324 | 72723 | 17.981 |
| 3 | 23.341 | 407790 | 12860 | 3.516 |
| Total | | 11597432 | 438058 | |

TABLE 2

Peak Analysis Data - Chromatogram 2

| Peak | Retention Time (min) | Area | Height | Concentration (%) |
|---|---|---|---|---|
| 1 | 18.397 | 10870932 | 423474 | 78.020 |
| 2 | 20.762 | 2562448 | 89011 | 18.391 |
| 3 | 23.304 | 500083 | 15788 | 3.589 |
| Total | | 13933463 | 528273 | |

The dried, filtered material was milled in a bead miller to provide an average particle size of 40±40 nm. The milled material was blended with maltodextrin to provide an 11 wt. % mixture of curcuminoids, and the blended material was sifted through a 40-mesh screen, subsequently through a 60-mesh screen, and finally through an 80-mesh screen. Product analysis results are shown in Table 3.

TABLE 3

Product Analysis

| Parameter | Result | Test Method |
|---|---|---|
| Moisture | 5.00000% | FCC $9^{th}$ Meditation, 1321-22 |
| Curcuminoid Content | 11.41000% | HPLC |
| Particle Size, 40 mesh | >99.00000% | ASTA Method No. 10.0 |
| Bulk Density | 0.38950 g/L | |
| Tapped Bulk Density | 0.4671 g/cc | ASTA 25.0, $IV^{th}$ Edition 1997 |
| T.P.C. | <10.0 cfu/g | BAM, online, January 2001, Chapter 3 |
| T.Y.M.C. | <10.0 cfu/g | BAM, online, April 2001, Chapter 18 |
| E. coli | <3.0 mpn/g | BAM, online, February 2013, Chapter 4 |
| Salmonella | Absent in 25 g | BAM, online, August 2012, Chapter 5 |

1 tbsp of dried curcuminoid product was stirred with 1 cup of water for 30 seconds to form a uniform suspension. The material remained suspended for over 1 hour.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method for preparing a curcuminoid composition suitable for mixing with an aqueous liquid for comestible applications, comprising:
   (a) providing a particulate curcuminoid source comprising turmeric root, the source having an average particle size within the range of about 1 mm to about 10 mm;
   (b) extracting curcuminoids from the particulate source into ethyl acetate;
   (c) removing at least a portion of the ethyl acetate to provide a curcuminoid slurry;
   (d) drying the curcuminoid slurry to provide a dried curcuminoid composition;
   (e) comminuting the dried curcuminoid composition; and
   blending the comminuted curcuminoid composition with a polysaccharide filler to yield a curcuminoid composition suitable for mixing with an aqueous liquid, the curcuminoid composition consisting of a total amount of curcuminoids within the range of about 15 wt. % to about 30 wt. % and the polysaccharide filler in an amount within the range of about 70 wt. % to about 85 wt. %.

2. The method of claim 1, wherein:
   (a) the curcuminoid source further comprises curcumin, demethoxycurcumin, bisdemethoxycurcumin, or a combination thereof.

3. The method of claim 2, wherein:
   (a) curcumin comprises about 75 wt. % to about 95 wt. % of the total curcuminoids present in the curcuminoid source;
   (b) demethoxycurcumin comprises about 1 wt. % to about 20 wt. % of the total curcuminoids present in the curcuminoid source; and
   (c) bisdemethoxycurcumin comprises about 0.5 wt. % to about 15 wt. % of the total curcuminoids present in the curcuminoid source.

4. The method of claim 1, wherein the particulate curcuminoid source has a D90 of at least about 1 mm.

5. The method of claim 1, wherein removing at least a portion of the ethyl acetate comprises evaporating a portion of the ethyl acetate to provide the curcuminoid slurry.

6. The method of claim 1, further comprising mixing the curcuminoid slurry with a non-polar wash solvent to remove oils from the slurry; and removing the wash solvent from the slurry.

7. The method of claim 1, wherein the curcuminoid slurry comprises at least about 10 wt. % curcuminoids.

8. The method of claim 1, wherein drying is performed at a temperature within the range of about 50° C. to about 100° C.

9. The method of claim 1, further comprising filtering the dried curcuminoid composition.

10. The method of claim 1, wherein the comminution is performed in a bead mill.

11. The method of claim 10, wherein the comminuted curcuminoid composition has average particle size within the range of about 40 nm to about 75 nm.

12. The method of claim 1, wherein the filler comprises maltodextrin having an average particle size within the range of about 20 nm to about 200 nm.

13. A method for preparing a curcuminoid composition suitable for mixing with an aqueous liquid for comestible applications, comprising:
   (a) providing a particulate curcuminoid source comprising turmeric root, the source having an average particle size within the range of about 1 mm to about 10 mm;
   (b) extracting curcuminoids from the particulate source into an extraction solvent;
   (c) removing at least a portion of the extraction solvent to provide a curcuminoid slurry;
   (d) mixing the curcuminoid slurry with a non-polar wash solvent to remove oils from the slurry;
   (e) drying the curcuminoid slurry to provide a dried curcuminoid composition;
   (f) comminuting the dried curcuminoid composition in a bead mill to provide a nanoparticulate curcuminoid composition having an average particle size within the range of about 5 nm to about 75 nm; and
   blending the nanoparticulate curcuminoid composition with a polysaccharide filler to yield a curcuminoid composition consisting of a total amount of curcuminoids within the range of about 15 wt. % to about 30 wt. % and the polysaccharide filler in an amount within the range of about 70 wt. % to about 85 wt. %.

14. A method for preparing a curcuminoid composition suitable for mixing with an aqueous liquid for comestible applications, comprising:
   (a) providing a particulate curcuminoid source comprising turmeric root, the source having an average particle size within the range of about 1 mm to about 10 mm;
   (b) extracting curcuminoids from the particulate source into an extraction solvent;
   (c) removing at least a portion of the extraction solvent to provide a curcuminoid slurry;
   (d) mixing the curcuminoid slurry with a non-polar wash solvent to remove oils from the slurry;
   (e) drying the curcuminoid slurry to provide a dried curcuminoid composition;
   comminuting the dried curcuminoid composition in a bead mill to provide a nanoparticulate curcuminoid composition having an average particle size within the range of about 40 nm to about 75 nm; and
   (g) blending the nanoparticulate curcuminoid composition with a polysaccharide filler to yield a curcuminoid composition consisting of a total amount of curcuminoids within the range of about 10 wt. % to about 30 wt. % and a polysaccharide filler in an amount within the range of about 70 wt. % to about 90 wt. %.

15. The method of claim 14, wherein the non-polar wash solvent is hexane.

16. The method of claim 14, wherein the extraction solvent is ethyl acetate.

17. The method of claim 14, wherein the curcuminoid composition consists of about 25 wt. % of curcuminoids and about 75 wt. % of the polysaccharide filler.

18. The method of claim 13, wherein the curcuminoid composition consists of about 25 wt. % of curcuminoids and about 75 wt. % of the polysaccharide filler.

* * * * *